United States Patent [19]

Beyer et al.

[11] Patent Number: 5,932,581
[45] Date of Patent: *Aug. 3, 1999

[54] METHOD OF REDUCING TISSUE DAMAGE ASSOCIATED WITH ISCHEMIA

[75] Inventors: Thomas A. Beyer, Old Lyme; Delvin R. Knight, Jr., Ledyard; Banavara L. Mylari, Waterford; Peter J. Oates, Gales Ferry; E. Roy Pettipher, Norwich; W. Ross Tracey, Niantic, all of Conn.

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/803,302

[22] Filed: Feb. 20, 1997

Related U.S. Application Data

[60] Provisional application No. 60/012,708, Feb. 28, 1996.

[51] Int. Cl.[6] .................................................. A61K 31/495
[52] U.S. Cl. .......................................................... 514/255
[58] Field of Search ............................................. 514/255

[56] References Cited

U.S. PATENT DOCUMENTS

| 5,138,058 | 8/1992 | Geisen et al. | 544/295 |
| 5,215,990 | 6/1993 | Geisen et al. | 514/255 |

FOREIGN PATENT DOCUMENTS

WO9407867  4/1994  WIPO .

OTHER PUBLICATIONS

Joseph R. Williamson et al., "Perspective in Diabetes, Hyperglycemic Pseudohypoxia and Diabetic Complications", Diabetes vol. 42, 801–813, Jun. 1993.

Diabetes, vol. 44,—Feb. 1995, pp. 234–242, XP000654520 Tilton et al.: "Inhibition of Sorbitol Dehydrogenase: Effects of Vascular and Neural Dysfunction in Streptozocin–induced Diabetic Rats".

Diabetologia, vol. 40, No. 3, 1997, pp. 271–281, XP002032766 Cameron et al.: "Comparison of the Effects of Inhibitors of Aldose Reductase and Sorbitol Dehydrogenase on Neurovascular Function, Nerve Conduction and Tissue Polyol Pathway Metabolites in Streptozocin–diabetic Rats:".

Arzneimittel–Forschun/Drug Research, vol. 44, No. 9, 1994, Main, Germany, pp. 1032–1043, XP000652228 Geisen Karl et al.: "Sorbitol–Accumulating Pyrimidine Derivatives."

Primary Examiner—Phyllis G. Spivack
Attorney, Agent, or Firm—Peter C. Richardson; Gregg C. Benson; A. Dean Olson

[57] ABSTRACT

A method of preventing tissue damage resulting from ischemia, comprising administering to a patient in need of such treatment an effective amount of a sorbitol dehydrogenase inhibitor.

20 Claims, No Drawings

METHOD OF REDUCING TISSUE DAMAGE ASSOCIATED WITH ISCHEMIA

This is a continuation of provisional application U.S. Ser. No. 60/012,708 filed Feb. 28, 1996, the benefit of which is hereby claimed under 37 C.F.R. §1.78(a)(3).

FIELD OF THE INVENTION

This invention relates to the use of sorbitol dehydrogenase inhibitors to reduce tissue damage resulting from ischemia in mammals, including human patients.

BACKGROUND OF THE INVENTION

Sorbitol dehydrogenase inhibitors constitute a class of compounds which have recently become known for their utility in preventing and treating conditions arising from complications of diabetes such as diabetic neuropathy. Such compounds are well known to those skilled in the art and readily identified by standard biological tests.

For example, PCT publication WO 94/07867 discloses methods of inhibiting sorbitol dehydrogenase and thus lowering fructose levels. The methods utilize certain substituted pyrimidines for the control of diabetic complications such as diabetic microangiopathy and diabetic macroangiopathy.

In addition, U.S. Pat. Nos. 5,215,990 and 5,138,058 disclose certain pyrimidine compounds having sorbitol dehydrogenase accumulating activity which are useful as reagents for a pharmacological screening model for testing aldose reductase inhibitors. In particular, U.S. Pat. No. 5,215,990 discloses as Example 2 the compound 4-[4-(N, N-dimethylsulfamoyl)piperazino]-2-hydroxymethylpyrimidine.

Joseph R. Williamson et al., "Perspectives in Diabetes, Hyperglycemic Pseudohypoxia and Diabetic Complications", Diabetes, Vol. 42, 801–813, June, 1993 discloses (FIG. 2) "parallels between functional consequences of an increased cystolic NADH/NAD$^+$ linked to hyperglycemic pseudohypoxia in diabetic tissues and hypoxia or ischemia in myocardial tissue".

SUMMARY OF THE INVENTION

This invention is directed to a method of reducing tissue damage (e.g., substantially preventing tissue damage, inducing tissue protection) resulting from ischemia. The method comprises administering to a mammal, including a human patient, in need of such treatment an amount of a sorbitol dehydrogenase inhibitor effective at reducing tissue damage.

A preferred aspect of this invention is a method of reducing heart damage resulting from myocardial ischemia.

Yet another preferred aspect of this invention is a method of reducing brain damage resulting from cerebral ischemia.

Yet another preferred aspect of this invention is a method of reducing liver damage resulting from hepatic ischemia.

Yet another preferred aspect of this invention is a method of reducing kidney damage resulting from renal ischemia.

Yet another preferred aspect of this invention is a method of reducing lung damage resulting from pulmonary ischemia.

Yet another preferred aspect of this invention is a method of reducing gastic damage resulting from gastric ischemia.

Yet another preferred aspect of this invention is a method of reducing intestinal damage resulting from intestinal ischemia.

Yet another preferred aspect of this invention is a method of reducing skeletal muscle damage resulting from skeletal muscle ischemia.

Yet another preferred aspect of this invention is a method of reducing spleen damage resulting from splenic ischemia.

Yet another preferred aspect of this invention is a method of reducing pancreas damage resulting from pancreatic ischemia.

Yet another preferred aspect of this invention is a method of reducing retinal damage resulting from retinal ischemia.

The term "reduction" is intended to include partial prevention or prevention which, although greater than that which would result from taking no drug or from taking placebo, is less than 100% in addition to substantially total prevention.

The term "damage resulting from [. . . ] ischemia" as employed herein refers to conditions directly associated with reduced blood flow to tissue, for example due to a clot or obstruction of blood vessels which supply blood to the subject tissue and which result, inter alia, in lowered oxygen transport to such tissue, impaired tissue performance, tissue dysfunction and necrosis.

Those skilled in the art will recognize that this invention also includes improvement of tissue performance (e.g., the ability to sustain normal muscle function is enhanced during ischemia). For example, a human could walk a further distance before having to stop from pain.

DETAILED DESCRIPTION OF THE INVENTION

Any sorbitol dehydrogenase inhibitor may be used as a compound (active agent) of this invention. The term sorbitol dehydrogenase inhibitor refers to compounds which inhibit the bioconversion of sorbitol to D-fructose catalyzed by the enzyme sorbitol dehydrogenase. Such inhibition is readily determined by those skilled in the are according to standard assays (N. E. Cameron, M. B. Leonard, I. S. Ross, P. H. Whiting, "The Effects of Sorbinil on Periperal Nerve Conduction Velocity, Polyol Concentrations and Morphology in the Streptozotocin-Diabetic Rat." Diabetologia, 29, 168–174, 1986). A variety of sorbitol dehydrogenase inhibitors are described and referenced below, however, other sorbitol dehydrogenase inhibitors will be known to those skilled in the art.

U.S. Pat. No. 5,138,058 (the disclosure of which is hereby incorporated by reference) discloses certain piperazine substituted pyrimidines having sorbitol accumulating activity.

U.S. Pat. No. 5,215,990 (the disclosure of which is hereby incorporated by reference) discloses certain pyrimidine derivatives having sorbitol accumulating activity.

In addition, PCT Publication No. WO9407867 discloses certain substituted pyrimidines as sorbitol dehydrogenase inhibitors. The compounds have the formula

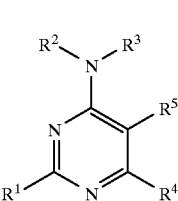

IA wherein $R^1$ is prodrugs of hydroxycarbonyl($C_1$–$C_6$)alkyl, ($C_1$–$C_6$)alkoxycarbonyl-($C_1$–$C_6$)alkyl, ($C_1$–$C_6$)alkyl-S—($C_1$–$C_6$)alkyl, ($C_1$–$C_6$)alkyl-SO—($C_1$–$C_6$)alkyl, ($C_1$–$C_6$)alkyl-SO$_2$—($C_1$–$C_6$)alkyl, dihydroxy-($C_1$–$C_6$)alkyl, aryl, heteroaryl, heteroaryl-($C_1$–$C_6$)alkyl, aryl-($C_1$–$C_6$)alkyl, ($C_1$-$C_6$)alkoxycarbonylaryl, aryl-($C_1$-$C_6$)alkyloxy or heteroaryl-($C_1$-$C_6$)alkyloxy, wherein said aryl and the aryl moieties of said aryl-($C_1$-$C_6$)alkyl, ($C_1$-$C_6$)alkoxycarbonylaryl, and aryl-($C_1$-$C_6$)alkyloxy are independently selected from phenyl and naphthyl, and wherein said heteroaryl and the heteroaryl moieties of said heteroaryl-($C_1$-$C_6$)alkyl and heteroaryl-($C_1$-$C_6$)alkyloxy are independently selected from pyridyl, furyl, tetrahydrofuryl, thienyl, imidazolyl, pyrazolyl, triazolyl, thiazolyl, oxazolyl and benzothiazolyl, and wherein said aryl and heteroaryl and the aryl and heteroaryl moieties of said heteroaryl-($C_1$-$C_6$)alkyl, aryl-($C_1$-$C_6$)alkyl, ($C_1$-$C_6$)alkoxycarbonylaryl, aryl-($C_1$-$C_6$)alkyloxy and heteroaryl-($C_1$-$C_6$)alkyloxy may optionally be substituted with one or more substituents independently selected from chloro, bromo, ($C_1$-$C_6$)alkyl, ($C_1$-$C_6$)alkoxy, —S—($C_1$-$C_6$)alkyl, —SO—($C_1$-$C_6$)alkyl, —$SO_2$—($C_1$-$C_6$)alkyl, hydroxy-($C_1$-$C_6$)alkyl and trifluoromethyl;

or $R^1$ is a group of the formula

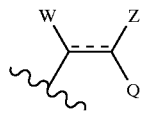

wherein the dotted line represents an optional double bond, W, Q and Z are independently selected from hydrogen, ($C_1$-$C_6$)alkyl and trifluoromethyl, phenyl, furyl, triazolyl, thiazolyl and thienyl, wherein said phenyl, furyl, triazolyl, thiazolyl and thienyl may optionally be substituted with one or more substituents, preferably with from zero to two substituents, independently selected from ($C_1$-$C_6$)alkyl, ($C_1$-$C_6$)alkoxy, trifluoromethyl and hydroxy;

or $R^1$ is a group of the formula

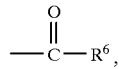

wherein $R^6$ is hydrogen, ($C_1$-$C_6$)alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents, preferably with from zero to two substituents, independently selected from chloro, bromo, nitro, trifluoromethyl, ($C_1$-$C_6$)alkoxy, —S—($C_1$-$C_6$)alkyl, —SO—($C_1$-$C_6$)alkyl and —$SO_2$—($C_1$-$C_6$)alkyl;

or $R^1$ is a group of the formula Y—O—CH—$R^7$, wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, ($C_1$-$C_6$)alkyl, ($C_1$-$C_6$)alkoxy, —S—($C_1$-$C_6$)alkyl, —SO—($C_1$-$C_6$)alkyl, —$SO_2$—($C_1$-$C_6$)alkyl and trifluoromothyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents, preferably with from zero to two substituents, independently selected from chloro, bromo, nitro, trifluoromethyl, ($C_1$-$C_6$) alkyl, ($C_1$-$C_6$)alkoxy, —S—($C_1$-$C_6$)alkyl, —SO—($C_1$-$C_6$) alkyl and —$SO_2$—($C_1$-$C_6$)alkyl;

$R^2$ and $R^3$ are independently selected from hydrogen, ($C_1$-$C_6$)alkyl, phenyl and phenyl-($C_1$-$C_4$)alkyl, wherein said phenyl and the phenyl moiety of said phenyl-($C_1$-$C_4$) alkyl may optionally be substituted with one or more substituents independently selected from ($C_1$-$C_6$)alkyl, ($C_1$-$C_6$) alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents, independently selected from ($C_1$-$C_6$)alkyl, —$CONH_2$, —$SO_2NH_2$, N-($C_1$-$C_4$) alkylsulfamoyl, N,N-di-($C_1$-$C_4$)alkylsulfamoyl, ($C_1$-$C_6$) alkoxycarbonyl, N,N-di-($C_1$-$C_4$)alkylcarbamoyl, N-($C_1$-$C_4$)-alkylcarbamoyl, N-phenylcarbamoyl, ($C_1$-$C_6$) alkylcarbonyl, phenylcarbonyl, ($C_1$-$C_6$)alkylsulfonyl, ($C_1$-$C_6$)alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents, independently selected from ($C_1$-$C_4$)alkyl, ($C_1$-$C_4$)alkoxy, chloro, bromo, nitro, amino, cyano and trifluoromethyl;

$R^4$ is hydrogen, chloro, bromo, cyano, nitro, trifluoromethyl, amino, ($C_1$-$C_6$)alkyl, ($C_1$-$C_6$) hydroxyalkyl, ($C_1$-$C_6$)alkoxy, phenyl, naphthyl or furyl, wherein said phenyl, naphthyl and furyl may optionally be substituted with one or more substituents, independently selected from chloro, bromo, trifluoromethyl, ($C_1$-$C_6$)alkyl, ($C_1$-$C_6$)alkoxy, —S—($C_1$-$C_6$)alkyl, —SO—($C_1$-$C_6$)alkyl, —$SO_2$—($C_1$-$C_6$)alkyl and hydroxy; and $R^5$ is hydrogen, ($C_1$-$C_6$)alkyl, ($C_1$-$C_6$)alkoxy, trifluoromethyl, ($C_1$-$C_6$)hydroxyalkyl, —S—($C_1$-$C_6$)alkyl, —SO—($C_1$-$C_6$)alkyl, —$SO_2$—($C_1$-$C_6$)alkyl, phenyl or furyl, wherein said phenyl and furyl may optionally be substituted with one or more substituents, independently selected from chloro, bromo, trifluoromethyl, ($C_1$-$C_6$)alkyl, ($C_1$-$C_6$)alkoxy, —SO—($C_1$-$C_6$)alkyl, —$SO_2$—($C_1$-$C_6$) alkyl and hydroxy;

or a pharmaceutically acceptable salt of such compound.

Other sorbitol dehydrogenase inhibitors disclosed by PCT Publication No. WO9407867 include compounds of the formula

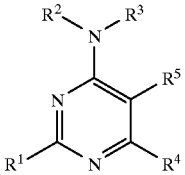

I wherein $R^1$ is hydrogen, $CF_3$, ($C_1$-$C_6$)alkyl, ($C_1$-$C_6$)alkyl-S—($C_1$-$C_6$)alkyl, ($C_1$-$C_6$)alkyl-SO—($C_1$-$C_6$)alkyl, ($C_1$-$C_6$)alkyl-$SO_2$—($C_1$-$C_6$)alkyl, hydroxy-($C_1$-$C_6$)alkyl, dihydroxy-($C_1$-$C_6$)alkyl, ($C_1$-$C_6$)alkoxy, ($C_1$-$C_6$) alkoxycarbonyl-($C_1$-$C_6$)alkyl, aryl selected from phenyl and naphthyl, aryl-($C_1$-$C_6$)alkyl wherein the aryl moiety is selected from phenyl and naphthyl, ($C_1$-$C_6$) alkoxycarbonylaryl wherein the aryl moiety is selected from phenyl and naphthyl, aryl-($C_1$-$C_6$)alkyl wherein the aryl moiety is selected from phenyl and naphthyl, aryl-($C_1$-$C_6$) alkyloxy wherein the aryl moiety is selected from phenyl and naphthyl, heteroaryl selected from pyridyl, furyl, tetrahydrofuryl, thienyl, imidazolyl, pyrazolyl, triazolyl, thiazolyl, oxazolyl, benzothiazolyl, benzofuranyl, and benzothienyl; heteroaryl-($C_1$–$C_6$)alkyl wherein heteroaryl is defined as above, or heteroaryl-($C_1$–$C_6$)alkyloxy wherein heteroaryl is defined as above, and wherein said aryl and heteroaryl groups, the aryl moieties of said aryl-($C_1$–$C_6$) alkyl, ($C_1$–$C_6$)alkoxycarbonylaryl and aryl-($C_1$–$C_6$) alkyloxy and the heteroaryl moiety of said heteroaryl-($C_1$–$C_6$)alkyl may optionally be substituted with one or more substituents independently selected from chloro, bromo, ($C_1$–$C_6$)alkyl, ($C_1$–$C_6$)alkoxy, —S—($C_1$–$C_6$)alkyl, —SO—($C_1$–$C_6$)alkyl, —SO$_2$—($C_1$–$C_6$)alkyl, hydroxy-($C_1$–$C_6$)alkyl and trifluoromethyl;

or $R^1$ is a group of the formula

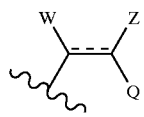

wherein the dotted line represents an optional double bond, W, Q and Z are independently selected from hydrogen, ($C_1$–$C_6$)alkyl and trifluoromethyl, phenyl, furyl, triazolyl, thiazolyl and thienyl, wherein said phenyl, furyl, triazolyl, thiazolyl and thienyl may optionally be substituted with one or more substituents independently selected from ($C_1$–$C_6$) alkyl, ($C_1$–$C_6$)alkoxy, trifluoromethyl and hydroxy;

or $R^1$ is a group of the formula

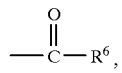

wherein $R^6$ is hydrogen, ($C_1$–$C_6$)alkyl, aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl and benzothienyl, wherein said aryl and heteroaryl groups may optionally be substituted with one or more substituents independently selected from chloro, bromo, nitro, trifluoromethyl, ($C_1$–$C_6$) alkoxy, —S—($C_1$–$C_6$)alkyl, —SO—($C_1$–$C_6$)alkyl and —SO$_2$—($C_1$–$C_6$)alkyl;

or $R^1$ is a group of the formula Y—O—CH—$R^7$, wherein $R^7$ is aryl selected from phenyl and naphthyl, or heteroaryl selected from pyridyl, furyl, thienyl, imidazolyl, pyrazolyl, triazolyl, thiazolyl, oxazolyl, benzothiazolyl, benzofuranyl, benzothienyl and quinolyl, wherein said aryl and heteroaryl groups may optionally be substituted with one or more substituents, preferably with from zero to two substituents, independently selected from chloro, bromo, ($C_1$–$C_6$)alkyl, ($C_1$–$C_6$)alkoxy, —S—($C_1$–$C_6$)alkyl, —SO—($C_1$–$C_6$alkyl, —SO$_2$—($C_1$–$C_6$)alkyl and trifluoromethyl, and Y is hydrogen, benzyl, acetyl, benzoyl, aryl selected from phenyl and naphthyl, heteroaryl selected from furyl, thienyl, thiazolyl and oxazolyl, wherein said aryl and heteroaryl groups may optionally be substituted with one or more substituents independently selected from chloro, bromo, nitro, trifluoromethyl, ($C_1$–$C_6$)alkyl, ($C_1$–$C_6$)alkoxy, —S— ($C_1$–$C_6$)alkyl, —SO—($C_1$–$C_6$)alkyl and —SO$_2$—($C_1$–$C_6$) alkyl; $R^2$ and $R^3$ are independently selected from hydrogen, ($C_1$–$C_6$)alkyl, phenyl and phenyl-($C_1$–$C_4$)alkyl, wherein said phenyl and the phenyl moiety of said phenyl —($C_1$–$C_4$) alkyl may optionally be substituted with one or more substituents independently selected from ($C_1$–$C_6$)alkyl, ($C_1$–$C_6$) alkoxy, chloro, bromo and trifluoromethyl;

or $R^2$ and $R^3$ form, together with the nitrogen to which they are attached, a cyclic group selected from azetidino, pyrrolidino, piperidino, piperazino and morpholino, wherein said cyclic group may optionally be substituted with from zero to two substituents, independently selected from ($C_1$–$C_6$)alkyl, —CONH$_2$—, —SO$_2$NH$_2$, N—($C_1$–$C_4$) alkylsulfamoyl, N,N-di-($C_1$–$C_4$)alkylsulfamoyl, ($C_1$–$C_6$) alkoxycarbonyl, N,N-di-($C_1$–$C_4$)alkylcarbamoyl, N-($C_1$–$C_4$)alkylcarbamoyl, N-phenylcarbamoyl, ($C_1$–$C_6$) alkylcarbonyl, phenylcarbonyl, ($C_1$–$C_6$)alkylsulfonyl, ($C_1$–$C_6$)alkylsulfinyl, phenylsulfonyl, heteroarylsulfonyl and heteroarylcarbonyl, wherein the heteroaryl moieties of said heteroarylcarbonyl and heteroarylsulfonyl are selected from furyl, thienyl, thiazolyl, and oxazolyl, and wherein the phenyl moieties of said phenylcarbonyl, N-phenylcarbamoyl, phenylcarbonyl and phenylsulfonyl may optionally be substituted with one or more substituents independently selected from ($C_1$–$C_4$)alkyl, ($C_1$–$C_4$)alkoxy, chloro, bromo, nitro, amino, cyano and trifluoromethyl;

$R^4$ is hydrogen, chloro, bromo, cyano, nitro, trifluoromethyl, amino, ($C_1$–$C_6$)alkyl, ($C_1$–$C_6$) hydroxyalkyl, ($C_1$–$C_6$)alkoxy, phenyl, naphthyl or furyl, wherein said phenyl, naphthyl and furyl may optionally be substituted with one or more substituents independently selected from chloro, bromo, trifluoromethyl, ($C_1$–$C_6$)alkyl, ($C_1$–$C_6$)alkoxy, —S—($C_1$–$C_6$)alkyl, —SO—($C_1$–$C_6$)alkyl, —SO$_2$—($C_1$–$C_6$)alkyl and hydroxy; and $R^5$ is hydrogen, ($C_1$–$C_6$)alkyl, ($C_1$–$C_6$)alkoxy, trifluoromethyl, ($C_1$–$C_6$)hydroxyalkyl, —S—($C_1$–$C_6$)alkyl —SO—($C_1$–$C_6$)alkyl, —SO$_2$—($C_1$–$C_6$)alkyl, phenyl or furyl, wherein said phenyl and furyl may optionally be substituted with one or more substituents independently selected from chloro, bromo, trifluoromethyl, ($C_1$–$C_6$)alkyl, ($C_1$–$C_6$)alkoxy, —SO—($C_1$–$C_6$)alkyl, —SO$_2$—($C_1$–$C_6$) alkyl and hydroxy;

or a pharmaceutically acceptable salt thereof.

The compounds described above are readily available or can be easily synthesized by those skilled in the art using conventional methods of organic synthesis particularly in view of the pertinent patent and patent application specification descriptions.

Some sorbitol dehydrogenase inhibitors have asymmetric carbon atoms and therefore are enantiomers or diastereomers. Diasteromeric mixtures can be separated into their individual diastereomers on the basis of their physical chemical differences by methods known per se, for example, by chromatography and/or fractional crystallization.

Some sorbitol dehydrogenase inhibitors are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

Some sorbitol dehydrogenase inhibitors are basic and they form a salt with a pharmaceutically acceptable anion. All such salts are within the scope of this invention and they can be prepared by conventional methods. For example, they can be prepared simply by contacting the acidic and basic entitles, usually in a stoichiometric ratio, in ether an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention form hydrates or solvates and they are also within the scope of the invention.

The activity and thus utility of the compounds of the present invention as medical agents in providing protection from ischemic damage to tissue in a mammal can be demonstrated by the activity of the compounds in the in vitro assay described herein-below. This assay is more particularly directed to providing protection from ischemic damage to myocardial tissue (e.g., for inducing cardioprotection). The assay also provides a means whereby the activities of the compounds of this invention can be compared with the activities of other known compounds. The results of these comparisons are useful for determining dosage levels in mammals, including humans, for inducing protection from ischemia particularly in the myocardium.

Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described following demonstrates that a test compound (i.e., a compound as claimed herein) can also pharmacologically induce cardioprotection, i.e., reduced myocardial infarct size, when administered to a rabbit isolated heart. The effects of the test compound are compared to ischemic preconditioning and the A1/A3 adenosine agonist, APNEA ($N^6$-[2-(4-aminophenyl)ethyl]adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a branch of the left anterior descending coronary artery, approximately ⅔ of the distance towards the apex of the heart. The heart is removed from the chest and rapidly (<30 cc) mounted on a Langendorff apparatus. The heart is retrogradely used via the aorta in a non-recirculating manner with a modified Krebs solution (NaCl 118.5 mM, KCl 4.7 mM, Mg $SO_4$1.2 mM, $KH_2PO_4$ 1.2 mM, $NaHCO_3$24.8 mM, $CaCl_2$2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure $\leq$10 mmHg. Perfusate flow rates are routinely determined throughout the experimental period.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at ≈200 bpm for the remainder of the experiment. Ischemic preconditioning is induced by total cessation of cardiac perfusion (global ischemia) for 5 min, followed by reperfusion for 10 min. The global ischemia/reperfusion is repeated one additional time, followed by a 30 min regional ischemia. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts which receive test compounds do not undergo the two periods of ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$M) is perfused through the heart; this stains all of the myocardium, except that area at risk for infarct development (area-at-risk). The heart is removed from the Langendorff apparatus, blotted dry, weighed, wrapped in aluminum foil and stored overnight at −20° C. The next day, the heart is sliced into 2 mm transverse sections from the apex to just above the coronary artery snare. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for difference in the area-at-risk between hearts, the data is expressed as the ratio of infarct area vs. area-at-risk (%IA/AAR).

The activity and thus utility of the compounds of the present invention as medical agents in providing protection from ischemic damage to tissue in a mammal can be further demonstrated by the activity of the compounds in the in vitro assay described herein below. The assay also provides a means whereby the activities of the compounds of this invention can be compared with the activities of other known compounds. The results of these comparisons are useful for determining dosage levels in mammals, including humans, for inducing protection from ischemia.

The activity of a sorbitol dehydrogenase inhibitor in a tissue can be determined by testing the amount of sorbitol dehydrogenase inhibitor that is required to raise tissue sorbitol (i.e., by inhibit the further metabolism of sorbitol consequent to blocking sorbitol dehydrogenase) or lower tissue fructose (by inhibiting its production from sorbitol consequent to blocking sorbitol dehydrogenase). While not wishing to be bound by any particular theory or mechanism, it is believed that a sorbitol dehydrogenase inhibitor, by inhibiting sorbitol dehydrogenase, prevents or reduces ischemic damage as described hereinafter in the following paragraph and scheme.

When the supply of oxygenated blood to a tissue is interrupted or slowed down (ischemia) the cells in the oxygen-deficient tissue derive their energy (ATP) from glucose via glycolysis (which does not require the presence of oxygen). Glycolysis also requires a supply of $NAD^+$ and in an ischemic tissue the length of time glycolysis can be maintained becomes sensitive to the supply of NAD$^+$. However, sorbitol dehydrogenase (SDH) also utilizes NAD$^+$ but does not produce an increase in ATP. Thus, it follows that preventing or retarding NAD$^+$ use by SDH with sorbitol dehydrogenase inhibitors (SDIs) will enhance or prolong the ability of ischemic tissue to carry out glycolysis, i.e., to produce energy in the absence of oxygen and in turn enhance and prolong the survival of the cells in the tissue. Since, inhibition of SDH will retard depletion of the tissue's NAD$^+$, a sorbitol dehydrogenase inhibitor is an effective anti-ischemic agent.

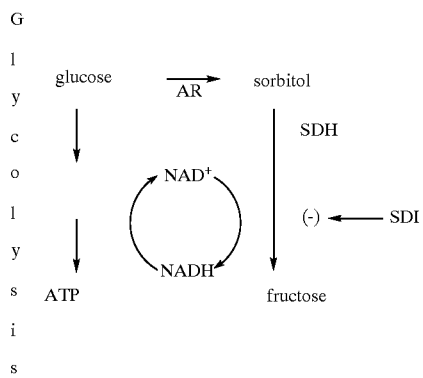

Again, the activity of a sorbitol dehydrogenase inhibitor can be determined by the amount of sorbitol dehydrogenase inhibitor that is required to raise tissue sorbitol or lower tissue fructose.

Male Sprague-Dawley rats are rendered diabetic by injection of streptozocin at 55 mg/kg, i.v., in pH 4.5 citrate buffer. They are fed ad libitum in controlled conditions of housing, temperature and lighting. After five weeks of diabetes, the rats are anesthetized with an overdose of pentobarbital, and tissues are rapidly removed and analyzed for sorbitol and fructose.

Sorbitol levels are analyzed according to the method of Donald M. Eades et al., "Rapid Analysis of Sorbitol, Galactitol, Mannitol and Myoinositol Mixtures From Biological Sources", *Journal of Chromatography*, 490, 1–8, (1989).

Fructose in rat tissues is enzymatically measured using a modification of the method of Ameyama (*Methods in Enzymology*, 89:20–29 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contains 0.1 ml neutralized 6% perchloric acid nerve extract in a final volume of 1.5 ml. Following incubation for 60 minutes at room temperature in a closed drawer, sample fluorescence is determined at excitation=560 nm, emission=580 nm with slits of 5 mm each on a Perkin-Elmer model 650-40 fluorescence spectrophotometer. Fructose concentrations are calculated by comparison with a series of known fructose standards.

The sorbitol dehydrogenase inhibitor compounds of this invention are thus useful in reducing or minimizing damage effected directly to any tissue that may be susceptible to ischemia/reperfusion injury (e.g., heart, brain, lung, kidney, liver, gut, skeletal muscle, retina) as the result of an ischemic event (e.g., myocardial infarction). The active compound is therefore usefully employed prophylactically to prevent, i.e. (prospectively or prophylactically) to blunt or stem, tissue damage (e.g., myocardial tissue) in patients who are at risk for ischemia (e.g., myocardial ischemia).

The sorbitol dehydrogenase inhibitor compounds of this invention are particularly well suited to the treatment of diabetic patients because of increased metabolism through sorbitol dehydrogenase in the diabetic state. The compounds of this invention are also well suited for prophylactic use with non-diabetic patients who have actually suffered or who are considered at risk of suffering from ischemic events (e.g., myocardial ischemia).

Administration of the compounds of this invention can be via any method which delivers the sorbitol dehydrogenase inhibitors to the desired tissue. These methods include topical, oral routes, parenteral, intraduodenal routes etc.

Thus, for example, in one mode of administration the sorbitol dehydrogenase inhibitor of this invention may be administered just prior to cardiac surgery (e.g., within twenty-four hours of surgery) where there is risk of myocardial ischemia. In an alternative exemplary mode, the compounds may be administered subsequent to cardiac surgery (e.g., within twenty-four hours after surgery) where there is risk of myocardial ischemia. The compounds of this invention may also be administered in a chronic daily mode. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the effect that the attending physician considers appropriate for the patient. In considering the degree of sorbitol dehydrogenase inhibitor activity desired, the physician must balance a variety of factors such as the target tissue, severity of the disease/condition and age of the patient.

An amount of the sorbitol dehydrogenase inhibitor of this invention that is effective for ischemic protection is used. Typically, an effective dosage for the sorbitol dehydrogenase inhibitors of this invention is in the range of about 0.1 mg/kg/day to 100 mg/kg/day in single or divided doses, preferably 0.1 mg/kg/day to 20 mg/kg/day in single or divided doses.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug (e.g., due to age or surgical state). For certain tissues such as the eye, topical administration may also be suitable.

The compounds of the present invention are generally administered in the form of a pharmaceutical composition comprising at least one sorbitol dehydrogenase inhibitor together with a pharmaceutically acceptable vehicle or diluent. Thus, the compounds can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compound of this invention can be combined with various sweetening agents, flavoring agents, coloring agents, emulsifying agents and/or suspending agents, as well as such diluents as water, ethanol, propylene glycol, glycerin and various like combinations thereof.

For purpose of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Transdermal or intracranial (e.g., topical) compositions may be prepared by those skilled in the art.

Methods of preparing various pharmaceutical compositions with a certain amount of active ingredient are known, or will be apparent in light of this disclosure, to those skilled in this art. For examples, see *Remington's Pharmaceutical Sciences,* Mack Publishing Company, Easton, Pa., 15th Edition (1975).

Pharmaceutical compositions according to the invention may contain 0.01%–95% of the compound(s) of this invention, preferably 1%–70%. In any event, the composition or formulation to be administered will contain a quantity of a compound(s) according to the invention in an amount effective to treat the signs of the subject being treated, i.e., protection from ischemic damage.

EXAMPLE 1

Male New Zealand White rabbits (3–4 kg) (control group, n=6; preconditioned group, n=6; APNEA-treated group, n=9; 4-[4-(N,N-Dimethylsulfamoyl)piperazino]-2-hydroxymethylpyrimidine-treated group, n=8 at 5 $\mu$M, n=6 at 50 $\mu$M and n=7 at 200 $\mu$M) were anesthetized with sodium pentobarbital (30 mg/kg, i.v.). After deep anesthesia was achieved (determined by the absence of an ocular blink reflex) the animal was intubated and ventilated with 100% $O_2$ using a positive pressure ventilator. A left thoracotomy was performed, the heart exposed, and a snare (2-0 silk) placed loosely around a branch of the left anterior descending coronary artery, approximately ⅔ of the distance towards the apex of the heat. The heart was removed from the chest and rapidly (<30 sec) mounted on a Langendorff apparatus. The heart was retrogradely perfused via the aorta in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), hereinafter referred to as Krebs solution, at a constant pressure of 80 mmHg and a temperature of 37° C. Perfusate pH was maintained at 7.4–7.5 by bubbling with 95% $O_2$/5% $CO_2$. Heart temperature was tightly controlled by using heated reservoirs for the physiological solution and water jacketing around both the perfusion tubing and the isolated heart. Heart rate and left ventricular pressures were determined via a latex balloon which was inserted in the left ventricle and connected by stainless steel tubing to a pressure transducer. The intraventricular balloon was inflated to provide a systolic pressure of 80–100 mmHg, and a diastolic pressure $\leq$10 mmHg. Perfusate flow rates were routinely determined throughout the experimental period. The hearts were allowed to equilibrate for 30 minutes before further manipulation, during which time they showed stable left ventricular pressures, as outlined above.

Hearts that were preconditioned were subjected to a five minute period of global ischemia (achieved by cross-clamping the aortic line) followed by ten minutes of reperfusion. This procedure was repeated a second time, after which the heart was subjected to 30 minutes of regional ischemia (provided by tightening the snare around the coronary artery branch) and a 120 minute period of reperfusion (accomplished by releasing the coronary artery snare).

In hearts that were treated with the A1/A3 agonist APNEA, the drug (500 nM, in Krebs solution) was perfused through the heart via the aorta for five minutes, followed by 10 minutes of perfusion with drug-free Krebs solution. The hearts were then subjected to 30 minutes of ischemia and 120 minutes of reperfusion, as described above.

In hearts that were treated with the test compound, 4-[4-(N,N-dimethylsulfamoyl)piperazino]-2-hydroxymethyl pyrimidine (5, 50 and 200 $\mu$M in Krebs solution), the drug was perfused through the heart via the aorta for a period which began 30 minutes prior to the 30 minute regional ischemia and continued throughout the ischemia and reperfusion periods described above (total perfusion time: 3 hours).

Control hearts were subjected to the 30 minutes of regional ischemia and 120 minutes of reperfusion, with no other treatments.

At the end of the 120 min reperfusion period, the coronary artery snare was again tightened, and a 0.5% suspension in Krebs solution of fluorescent zinc cadmium sulfate particles (1–10 $\mu$M) perfused through the heart. The heart was then removed from the Langendorff apparatus, blotted dry, weighed, wrapped in aluminum foil and stored overnight at −20° C. The next day, each heart was sliced into 5–7 2 mm transverse sections from the apex to just above the coronary artery snare. The slices were stained with 1% triphenyl tetrazolium chloride (TTC) in phosphate-buffered saline for 20 min at 37° C. The infarcted area (no stain) and the area-at-risk (no fluorescent particles) were calculated for each slice of left ventricle using a precalibrated image analyzer. To normalize the ischemic injury for differences in the area-at-risk between hearts, the data was expressed as the ratio of infarct area vs. area-at-risk (%IA/AAR).

The results from the above in vitro test are detailed in the following Table 1. The results demonstrate that the test compound induced significant cardioprotection relative to the control group.

TABLE 1

| Treatment | n | Infarct Area/ Area-at-Risk | Standard Error |
|---|---|---|---|
| Control | 14 | 63.5 | 4.1 |
| Preconditioned | 10 | 11.3 | 2.7 |
| APNEA (500 nM) | 9 | 19.0 | 3.6 |
| 4-[4-(N,N-dimethyl-(5 $\mu$M)sulfamoyl)piperazino]-2-hydroxymethyl pyrimidine (5 $\mu$M) | 8 | 48.5 | 4.2 |
| 4-[4-(N,N-dimethyl-(50 $\mu$M)sulfamoyl)piperazino]-2-hydroxymethyl pyrimidine (50 $\mu$M) | 6 | 39.0 | 2.7 |
| 4-[4-(N,N-dimethyl-(200 $\mu$M)sulfamoyl)piperazino]-2-hydroxymethyl pyrimidine (200 $\mu$M) | 7 | 38.7 | 5.9 |

EXAMPLE 2

Male Sprague-Dawley rats were rendered diabetic by injection of streptozocin at 55 mg/kg, i.v., in pH 4.5 citrate buffer. They were fed ad libitum in controlled conditions of housing, temperature and lighting. After five weeks of diabetes, the rats were anesthetized with an overdose of pentobarbital, and tissues were rapidly removed and analyzed for sorbitol and fructose by methods cited above.

Sorbitol levels were analyzed according to the method of Donald M. Eades et al., "Rapid Analysis of Sorbitol, Galactitol, Mannitol and Myoinositol Mixtures From Biological Sources", *Journal of Chromatography*, 490, 1–8, (1989).

Fructose in rat tissues was enzymatically measured using a modification of the method of Ameyama (*Methods in Enzymology*, 89, 1982), in which ferricyanide was replaced by resazurin, a dye that is reduced to the highly fluorescent resorufin. The amount of resorufin fluorescence is stoichiometric with the amount of fructose oxidized by fructose dehydrogenase. The assay contained 0.1 ml neutralized 6% perchloric acid nerve extract in a final volume of 1.5 ml. Following incubation for 60 minutes at room temperature in a closed drawer, sample fluorescence was determined at excitation=560 nm, emission=680 nm with slits of 5 mm each in a Perkin-Elmer model 650-40 fluorescence spectrophotometer. Fructose concentrations were calculated by comparison with a series of known standards containing 0 to 200 ng fructose per assay.

Table 2 details the elevation of tissue sorbitol in a variety of tissues and thus the inhibition of sorbitol dehydrogenase and consequently the anti-ischemic activity of the sorbitol dehydrogenase inhibitor 4-[4-(N,N-dimethylsulfamoyl)piperazino]-2-hydroxymethyl pyrimidine. Table 3 details the lowered tissue fructose in a variety of tissues and thus the inhibition of sorbitol dehydrogenase and consequently the anti-ischemic activity of the sorbitol dehydrogenase inhibitor 4-[4-(N,N-dimethylsulfamoyl)piperazino]-2-hydroxymethyl pyrimidine.

TABLE 3

Effects of 4-[4-(N,N-dimethylsulfamoyl)piperazino]-2-hydroxymethyl pyrimidine (SDI) (200 mg/kg bw/day) on Retina, Sciatic nerve, and Lens sorbitol and fructose levels (nmole/g) in rats with diabetes of 5 weeks duration

|  | Retina | | Sciatic Nerve | | Lens | |
| --- | --- | --- | --- | --- | --- | --- |
|  | Sor | Fru | Sor | Fru | Sor | Fru |
| Control | 126 | 76 | 159 | 814 | 436 | 983 |
|  | (75) | (14) | (55) | (197) | (73) | (151) |
| +SDI | 574 | 75 | 2050 | 425 | 5410 | 998 |
|  | (161) | (48) | (697) | (201) | (1848) | (207) |
| Diabetic | 1409 | 1289 | 1863 | 5815 | 37006 | 12676 |
|  | (412) | (178) | (623) | (1711) | (6064) | (1261) |
| +SDI | 5381 | 534 | 9975 | 1382 | 48028 | 2700 |
|  | (1702) | (224) | (4397) | (1358) | (8513) | (1296) |

* Mean ± SD (N = 8–13)
( ) numbers in parenthesis are standard deviation

It should be understood that the invention is not limited to the particular embodiments described herein, but that various changes and modifications may be made without departing from the spirit and scope of this novel concept as defined by the following claims.

We claim:

1. A method of reducing tissue damage resulting from ischemia comprising administering to a mammal in need of said treatment an amount of a sorbitol dehydrogenase inhibitor effective at reducing ischemic damage wherein said ischemia is a result of an etiology independent of diabetic microangiopathy or diabetic macroangiopathy.

2. A method as recited in claim 1 wherein the tissue is heart, brain, liver, kidney, lung, gut, skeletal muscle, spleen, pancreas, retina or intestinal tissue.

TABLE 2

Effects of 4-[4-(N,N-dimethylsulfamoyl)piperazino]-2-hydroxymethyl pyrimidine (SDI) 200 mg/kg bw/day) on sorbitol levels (nmole/g) in rats with diabetes at 5 weeks duration

|  | AU | PU | RET | BRN | SN | LENS | AOR | MSL | HRT |
| --- | --- | --- | --- | --- | --- | --- | --- | --- | --- |
| Control | 14 | 7 | 126 | 126 | 159 | 436 | 11 | 18 | 72 |
|  | (17) | (11) | (75) | (82) | (55) | (73) | (12) | (13) | (37) |
| +SDI | 254 | 289 | 574 | 168 | 2050 | 5410 | 61 | 33 | 73 |
|  | (124) | (78) | (161) | (82) | (697) | (1848) | (22) | (20) | (39) |
| Diabetic | 915 | 601 | 1409 | 192 | 1863 | 37006 | 60 | 25 | 177 |
|  | (371) | (282) | (412) | (70) | (623) | (6064) | (19) | (16) | (86) |
| +SDI | 3426 | 2379 | 5380 | 901 | 9975 | 48020 | 103 | 68 | 270 |
|  | (1778) | (1160) | (1702) | (591) | (4397) | (8513) | (65) | (24) | (116) |

* Mean ± SD (N = 9–13)
AU = anterior uvea
PU = posterior uvea
RET = retina
BRN = brain
SN = sciatic nerve
( ) numbers in parenthesis are standard deviation
LENS = lens
AOR = aorta
MSL = muscle
HRT = heart 3. A method as recited in claim 2 wherein said mammal is a human.

4. A method as recited in claim 3 wherein said tissue is heart tissue.

5. A method as recited in claim 3 wherein said tissue is brain tissue.

6. A method as recited in claim 3 wherein said tissue is liver tissue.

7. A method as recited in claim 3 wherein said tissue is kidney tissue.

8. A method as recited in claim 3 wherein said tissue is lung tissue.

9. A method as recited in claim 3 wherein said tissue is gut tissue.

10. A method as recited in claim 3 wherein said tissue is skeletal muscle tissue.

11. A method as recited in claim 3 wherein said tissue is spleen tissue.

12. A method as recited in claim 3 wherein said tissue is pancreas tissue.

13. A method as recited in claim 3 wherein said tissue is retina tissue.

14. A method as recited in claim 3 wherein said tissue is intestinal tissue.

15. A method as recited in claim 3 wherein said inhibitor is 4-{4-(N,N-dimethylsulfamoyl)piperazino}-2-hydroxymethylpyrimidine.

16. A method as recited in claim 15 wherein the effective amount of sorbitol dehydrogenase inhibitor is about 0.1 mg/kg/day to about 100 mg/kg/day.

17. A method as recited in claim 3 wherein the effective amount of sorbitol dehydrogenase inhibitor is about 0.1 mg/kg/day to about 100 mg/kg/day.

18. A method as recited in claim 17 wherein said sorbitol dehydrogenase inhibitor is administered prophylactically.

19. A method as recited in claim 17 wherein said sorbitol dehydrogenase inhibitor is administered prior to cardiac surgery.

20. A method as recited in claim 17 wherein said sorbitol dehydrogenase inhibitor is administered chronically.

* * * * *